US012728266B2

(12) United States Patent
Segovia Martinez et al.

(10) Patent No.: US 12,728,266 B2
(45) Date of Patent: Sep. 8, 2026

(54) HARMONIC ALLOCATION OF COCHLEA IMPLANT FREQUENCIES

(71) Applicant: Cochlear Limited, Macquarie University (AU)

(72) Inventors: Manuel Segovia Martinez, Vallauris (FR); Waldo Nogueira Vazquez, Vallauris (FR)

(73) Assignee: Cochlear Limited, Macquarie University (AU)

( * ) Notice: Subject to any disclaimer, the term of this patent is extended or adjusted under 35 U.S.C. 154(b) by 1317 days.

(21) Appl. No.: 17/352,644

(22) Filed: Jun. 21, 2021

(65) Prior Publication Data

US 2021/0393956 A1 Dec. 23, 2021

(30) Foreign Application Priority Data

Jun. 22, 2020 (EP) .................................... 20181474

(51) Int. Cl.
*A61N 1/36* (2006.01)
*A61N 1/05* (2006.01)

(52) U.S. Cl.
CPC ....... *A61N 1/36039* (2017.08); *A61N 1/0541* (2013.01)

(58) Field of Classification Search
None
See application file for complete search history.

(56) References Cited

U.S. PATENT DOCUMENTS

| | | | |
|---|---|---|---|
| 6,068,652 | A | 5/2000 | Cohen et al. |
| 8,027,733 | B1 | 9/2011 | Fridman et al. |
| 9,572,981 | B2 | 2/2017 | Noble et al. |

(Continued)

FOREIGN PATENT DOCUMENTS

| | | | |
|---|---|---|---|
| CN | 107921251 | A | 4/2018 |
| CN | 108175936 | A | 6/2018 |
| WO | WO 97/43871 | A1 | 11/1997 |

OTHER PUBLICATIONS

Franke-Trieger et al., "Estimation of insertion depth angle based on cochlea diameter and linear insertion depth: a prediction tool for the CI422", Eur Arch Otorhinolaryngol, 2015, vol. 272, pp. 3193-3199.

*Primary Examiner* — Erica S Lee
(74) *Attorney, Agent, or Firm* — Edell, Shapiro & Finnan, LLC

(57) ABSTRACT

An aspect of the disclosure is to provide a system and a method of fitting a cochlea implant system to a patient, the method including determining an insertion angle of at least one electrode of a first electrode array of the cochlea implant system inserted into a cochlea of the patient, determining a plurality of natural frequencies as a function of a cochlea spiral length based on a natural frequency allocation model and the insertion angle, determining a plurality of characteristic frequencies as a function of a cochlea spiral length by frequency downshifting the plurality of natural frequencies until an objective is obtained and while preserving the harmonic relationship between the natural frequencies of the plurality of natural frequencies in the plurality of characteristic frequencies, and allocating the plurality of characteristic frequencies to each electrode of the first electrode array based on the insertion angle of the at least one electrode.

20 Claims, 7 Drawing Sheets

(56) References Cited

U.S. PATENT DOCUMENTS

| | | | |
|---|---|---|---|
| 10,546,388 | B2 | 1/2020 | Noble et al. |
| 2011/0238176 | A1 | 9/2011 | Bradley et al. |
| 2016/0279412 | A1 | 9/2016 | Polak et al. |
| 2018/0161578 | A1 | 6/2018 | Baumann et al. |
| 2019/0167977 | A1* | 6/2019 | Risi ...................... A61N 1/0551 |
| 2022/0305268 | A1* | 9/2022 | Hassan .............. A61N 1/36117 |
| 2024/0249425 | A1 | 7/2024 | Agrawal et al. |

* cited by examiner

| Note name | Octaves | 1 | 2 | 3 | 4 | 5 |
|---|---|---|---|---|---|---|
| | B | 62 | 123 | 247 | 494 | 988 |
| | A sharp/B flat | 58 | 117 | 233 | 466 | 932 |
| | A | 55 | 110 | 220 | 440 | 880 |
| | G sharp/A flat | 52 | 104 | 208 | 415 | 831 |
| | G | 49 | 98 | 196 | 392 | 784 |

HARMONIC ALLOCATION OF COCHLEA IMPLANT FREQUENCIES

FIELD

The present disclosure relates to a method of fitting a cochlea implant system to a patient while preserving the harmonic relation between cochlea implant frequencies as in the frequencies of a normal hearing cochlea.

BACKGROUND

Using a current cochlea implant fitting procedure, the frequency allocation is normally using a standard allocation that does not consider the physiological frequency placing of a normal hearing cochlea.

A bimodal patient using a cochlea implant on a first ear and a normal hearing aid providing an acoustical stimulation on a second ear, and a single-sided patient using a cochlea implant on the first ear and is normal hearing on the second ear, will be introduced to a mismatch between the perception of the electrical stimulation provided by the cochlea implant to the first ear and the perception of the acoustic stimulation provided to the second ear with or without a normal hearing aid. The mismatch between the acoustic and the electrical stimulation will be perceived by the patient as the acoustic stimulation is coming from a sound source which is different from the electrical stimulation.

SUMMARY

An aspect of the disclosure is to provide a fitting system and a method of fitting a cochlea implant system to a patient for minimizing the mismatch in the way the patient is perceiving an electrical stimulation provided by a cochlea implant system at a first cochlea and the way the patient is perceiving the acoustic stimulation at a second cochlea.

A further aspect of the disclosure is to provide a simple way of performing the method which demands less computational power and less practical steps by a hearing aid dispenser.

A further aspect of the disclosure is to maintain for a patient using a cochlea implant system the harmonic relation between the allocated frequencies to an electrode array, and where the harmonic relation relates to a natural hearing person.

The aspect of the disclosure is achieved by a method of fitting a cochlea implant system to a patient. The method comprising determining an insertion angle of at least one electrode of a first electrode array of the cochlea implant system inserted into a cochlea of the patient. The determining of the insertion angle may be provided by performing a diagnostic medical imaging in which the implanted electrode array and anatomical structures of the cochlea are visible.

Furthermore, the method comprising determining a plurality of natural frequencies as a function of a cochlea spiral length based on a natural frequency allocation model and the insertion angle.

The plurality of natural frequencies as a function of a cochlea spiral length may be determined by determining an insertion angle for each of the electrodes of the first electrode array based on the insertion angle determined for the at least one electrode, and mapping the insertion angle of each electrodes of the first electrode array to a physiological model.

The physiological model may be based on Greenwood model (Greenwood, 1990).

When knowing the distances between each electrode of the electrode array relative to the at least one electrode for which the insertion angle is determined, the insertion angle of each electrode of the electrode array can easily be determined.

The plurality of natural frequencies as a function of a cochlea spiral length may be determined by determining an insertion angle for each of the electrodes of the first electrode array by performing a diagnostic medical imaging in which the implanted electrode array and anatomical structures of the cochlea are visible.

Furthermore, the method comprising determining a plurality of characteristic frequencies as a function of a cochlea spiral length by frequency downshifting the plurality of natural frequencies until an objective may be obtained and while preserving the harmonic relationship between the natural frequencies of the plurality of natural frequencies in the plurality of characteristic frequencies.

In some situations, it is important to preserve specific perceptual information of the acoustical signal (not frequency downshifted) after the frequency downshifting, and this is accomplished by introducing an objective to how much frequency downshifting is allowed.

The objective may be stored in a memory unit, and the amount of frequency downshifting relative to an objective may be stored in the memory unit.

Furthermore, the method comprising allocating the plurality of characteristic frequencies to each electrode of the first electrode array based on the insertion angle of the at least one electrode. Thereby, the cochlea implant system is fitted to the user.

Another aspect of the disclosure relates to a system for fitting a cochlea implant system to a patient comprising a first implantable stimulation unit with a first electrode array including a plurality of electrodes configured to apply an electrical stimulation to auditory nerve fibers of a cochlea of the patient, an external unit including a memory unit which comprises a natural frequency allocation model, a frequency allocating unit configured to allocate a plurality of characteristic frequencies to each electrode of the first electrode array according to a frequency allocating scheme.

The frequency allocating scheme including determining an insertion angle of at least one electrode of the first electrode array, determining a plurality of natural frequencies as a function of a cochlea spiral length based on the natural frequency allocation model and the insertion angle, determining the plurality of characteristic frequencies as a function of a cochlea spiral length by frequency downshifting the plurality of natural frequencies until an objective is obtained and while preserving the harmonic relationship between the natural frequencies of the plurality of natural frequencies in the plurality of characteristic frequencies, and allocating the plurality of characteristic frequencies to each electrode of the first electrode array based on the insertion angle of the at least one electrode.

The memory unit may be part of the cochlea implant system and/or a system for fitting a cochlea implant system.

The first implantable stimulation unit and the external unit may be part of the cochlea implant system or a fitting computer wired or wireless connected to the cochlea implant system. The external unit may be connected to the first implantable stimulation via a transcutaneously radio frequency interface applied into the external unit and in the first implantable stimulation unit.

In a further aspect the disclosure relates to the cochlea implant system which may be configured to continuously adapt the plurality of characteristic frequencies by dynamically changing the objective. The objective may be depended on the acoustic signal or a sound processing program of the cochlea implant system. The sound processing program may be set by an external device, e.g. a smartphone which is wirelessly connected to the cochlea implant system. Thereby, the electrode array of the cochlea implant system will always have an optimal frequency allocation in relation to the acoustical input received by the cochlea implant system. The acoustical input may be received by a microphone unit or an RF antenna. The microphone unit may include one or more microphones.

The objective may be one of following;

a first range of characteristic frequencies between 100 Hz and 250 Hz may be allocated to a most apical electrode of the first electrode array, a second range of characteristic frequencies between 6600 Hz and 8100 Hz may be allocated to a most basal electrode of the first electrode array, or that the frequency downshifting of the plurality of natural frequencies corresponds to one or more octaves.

By applying the objective to the most apical electrode, important perceptual information in low frequency is preserved after performing the frequency downshifting.

By applying the objective to the most basal electrode, important perceptual information in high frequency is preserved after performing the frequency downshifting.

By applying an octave restriction to the amount of frequency downshifting results in an improved perception and tactile interpretation of music as the patient will perceive the music with a harmonic relation between both cochleae.

The objective may be to obtain an octave shift in frequencies from one electrode to another electrode of the electrode array. Thereby, the patient will perceive music better than what is possible today.

An amount of frequency downshifting may relate to an insertion angle of a most apical electrode and the objective.

Thereby, an optimal frequency allocation is obtained relative to the position of the electrode array.

The insertion angle of a most apical electrode may be;

about 525 degrees, the frequency downshifting of the plurality of natural frequencies to the plurality of characteristic frequencies may be between ⅓ to ½, about 417 degrees, the frequency downshifting of the plurality of natural frequencies to the plurality of characteristic frequencies is between ⅕ to ½, or about 358 degrees, the frequency downshifting of the plurality of natural frequencies to the plurality of characteristic frequencies is between ⅙ to ⅕.

The method may further comprise determining an insertion angle of at least another electrode of a second electrode array of the cochlea implant system inserted into another cochlea of the patient, applying a stimulation pulse to at least one electrode of the first electrode array and the second electrode array simultaneously and time shifted for determining a binaural interaction component of the patient, and determining the plurality of natural frequencies as a function of a cochlea spiral length based on the binaural interaction component.

The plurality of characteristic frequencies may be determined for both the first and the second electrode array for obtaining a binaural interaction component for the patient to be compared with a binaural interaction component of normal hearing. The binaural interaction component of a normal hearing may be part of a natural frequency allocation model. The amount of frequency downshifting applied to both electrode arrays may either be the same or different when determining the binaural interaction component of the patient. The binaural interaction component of the patient is compared with the binaural interaction component of normal hearing, and an acceptable match criterion between the two binaural interaction components is determined by a standard deviation function, such as a root mean square function.

The amount of downshifting the plurality of natural frequencies may be determined by a natural binaural interaction component stored in the memory unit. The ideal amount of downshifting is when the binaural interaction component of the patient is similar to the natural binaural interaction component. The natural binaural interaction component may be an average of multiple other persons with normal hearing. Thereby, the binaural interaction component is determined while adjusting the frequency downshifting and stops when the binaural interaction component is similar to the natural binaural interaction component.

The binaural interaction component may be determined by the cochlea implant system or by a fitting computer of the system.

A first auditory brainstem response may be recorded by a recording electrode of the first electrode array when applying a first stimulation to the first cochlea by a stimulating electrode of the first electrode array, and then a second auditory brainstem response may be recorded by a recording electrode of the second electrode array when applying a second stimulation to the second cochlea by a stimulating electrode of the second electrode array. The second stimulation should be applied after a time period from a stimulation time of when the first stimulation was applied by the first stimulation electrode. A summed auditory brainstem response is determined by summing the first brainstem response and the second auditory brainstem response. Alternatively, the second auditory brainstem response may be time-shifted in relation to the first auditory brainstem with an interaural time difference before the summation. Then, a binaural waveform is recorded by the first and the second electrode array or by an external electrode applied on the top of the head and in-between the ears of the head of the patient when applying simultaneously a stimulation pulse via the stimulating electrode of both the first and the second electrode array. Binaural interaction component is determined by subtracting the binaural waveform with the summed auditory brainstem response.

The method may comprise determining another insertion angle of at least another electrode of the second electrode array, applying a stimulation pulse to at least one electrode of the first electrode array and the second electrode array simultaneously and time shifted for determining a binaural interaction component of the patient, determining the plurality of natural frequencies and another plurality of natural frequencies as a function of a cochlea spiral length based on the natural frequency allocation model, the binaural interaction component, and the insertion angle and the another insertion angle, respectively, determining the plurality of characteristic frequencies as a function of a cochlea spiral length by frequency downshifting the plurality of natural frequencies and determining another plurality of characteristic frequencies as a function of a cochlea spiral length by frequency downshifting the another plurality of natural frequencies until an objective is obtained and while preserving the harmonic relationship between the natural frequencies of the plurality of natural frequencies and the another plurality of natural frequencies in the plurality of characteristic frequencies and the another plurality of characteristic frequencies, respectively, and allocating the plurality of characteristic frequencies and the another plurality of characteristic frequencies to each electrode of the first and second electrode array, respectively.

Thereby, the patient will experience an improved perceive of binaural information in a cochlea implant system being bilateral, as the frequency allocated to each of the electrodes of the first electrode array and the second electrode array will be optimized to how a normal hearing perceives binaural information.

The method may comprise applying a stimulation pulse to at least one electrode of the first electrode array and an acoustical stimulation to another cochlea of the patient simultaneously and time shifted for determining a binaural interaction component of the patient, and determining the plurality of natural frequencies as a function of a cochlea spiral length based on the binaural interaction component.

The method may comprise determining applying a stimulation pulse to at least one electrode of the first electrode array and an acoustical stimulation to the another cochlea via a hearing aid simultaneously and time shifted for determining a binaural interaction component of the patient, determining the plurality of natural frequencies as a function of a cochlea spiral length based on the natural frequency allocation model, the binaural interaction component, and the insertion angle, determining the plurality of characteristic frequencies as a function of a cochlea spiral length by frequency downshifting the plurality of natural frequencies until an objective is obtained and while preserving the harmonic relationship between the natural frequencies of the plurality of natural frequencies in the plurality of characteristic frequencies, and allocating the plurality of characteristic to each electrode of the first electrode array, respectively.

Thereby, the patient will experience an improved perceive of binaural information in a cochlea implant system being bimodal, as the frequency allocated to each of the electrodes of the first electrode array will be optimized to how a normal hearing perceives binaural information.

The cochlea implant system may be of a bilateral type which includes an electrode array in both cochleae of the patient.

The cochlea implant system may be of a bimodal type which includes an electrode array in one cochlea and a hearing aid in the other cochlea of the patient.

The binaural interaction component may include multiple local maxima at different local maxima frequencies. The amount of frequency downshifting may be determined by harmonic relations between the different local maxima frequencies in relation to the harmonic relations between the plurality of natural frequencies. When the harmonic relations between different local maxima frequencies are similar to the harmonic relations between the natural frequencies of the plurality of natural frequencies, the amount of frequency downshifting is optimal.

The method may comprise determining an insertion angle of at least another electrode of a second electrode array of the cochlea implant system inserted into another cochlea of the patient, applying a stimulation pulse to at least one electrode of the first electrode array and the second electrode array for determining an interaural pulse time difference sensitivity or an interaural pitch matching of the patient, and determining the plurality of natural frequencies as a function of a cochlea spiral length based on the interaural pulse time difference sensitivity or the interaural pitch matching.

The system may comprise a filter bank configured to generate multiple audio bands, where each multiple audio band is mapped to each electrode of the electrode array, and where a frequency range of each of the multiple audio bands includes at least the plurality of characteristic frequencies allocated to the respective mapped electrode.

The memory unit of the cochlea implant system may include multiple objectives for respective acoustic environments which is detectable by a microphone unit or an RF antenna. Thereby, the cochlea implant system is configured to optimize continuously the allocation of the plurality of characteristic frequencies in relation to an acoustic environment of which the patient is within.

The cochlea implant system may be configured to receive a setting signal from an external device, such as a smartphone, via an RF antenna of the cochlea implant system, or the setting signal may be provided by the cochlea implant system by analyzing the acoustical signal. The setting signal may be used by the cochlea implant system for selecting a sound processing program which the external unit may use for determining an optimal sampling and/or coding strategy of the acoustic signal, and thereby, the external unit determines the amount of frequency downshifting and the natural frequency allocation model for obtaining an optimal allocation of the plurality of characteristic frequencies based on the sampling and coding strategy. The sampling and/or coding may be done by a sound processor of the external device.

The setting signal may be provided by the sound processor of the external device which is configured to analyze the coded acoustic signal for identifying at least fundamental frequencies and/or harmonic frequencies. The at least fundamental frequencies may be the setting signal which is used for determine the amount of frequency downshifting and the selection of the natural frequency allocation model from the memory.

The setting signal may be determined by the patient via the external device, or by a server connected to the external device and which uses the external device as an intermediate device for communicating with the cochlea implant system.

The setting signal may be determined automatically by an envelope analyzer of the external unit which determines the acoustic environment in combination with the microphone unit or the RF antenna.

The external unit may be a sound processor applied on the head of the patient and which is magnetically attracted by the implantable stimulation unit via a magnetic interface. Furthermore, the external unit may be applied on the ear. The implantable stimulation unit and the external unit are configured to communicate with each other via a transcutaneous radio frequency link.

The cochlea implant system may be fully implantable.

The method may be performed by the fitting computer, and/or the cochlea implant system and/or an external device, such as a smartphone, a tablet etc.

In another aspect, a method of fitting a cochlea implant system to a patient may comprise determining an insertion angle of at least one electrode of a first electrode array of the cochlea implant system inserted into a cochlea of the patient, determining a plurality of natural frequencies as a function of a cochlea spiral length based on a natural frequency allocation model and the insertion angle, determining a plurality of characteristic frequencies as a function of a cochlea spiral length while preserving the harmonic relationship between the natural frequencies of the plurality of natural frequencies in the plurality of characteristic frequencies, and allocating the plurality of characteristic frequencies to each electrode of the first electrode array based on the insertion angle of the at least one electrode.

Thereby, it is obtained a minimization of the mismatch in the way the patient is perceiving an electrical stimulation provided by a cochlea implant system at a first cochlea and the way the patient is perceiving the acoustic stimulation at a second cochlea.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
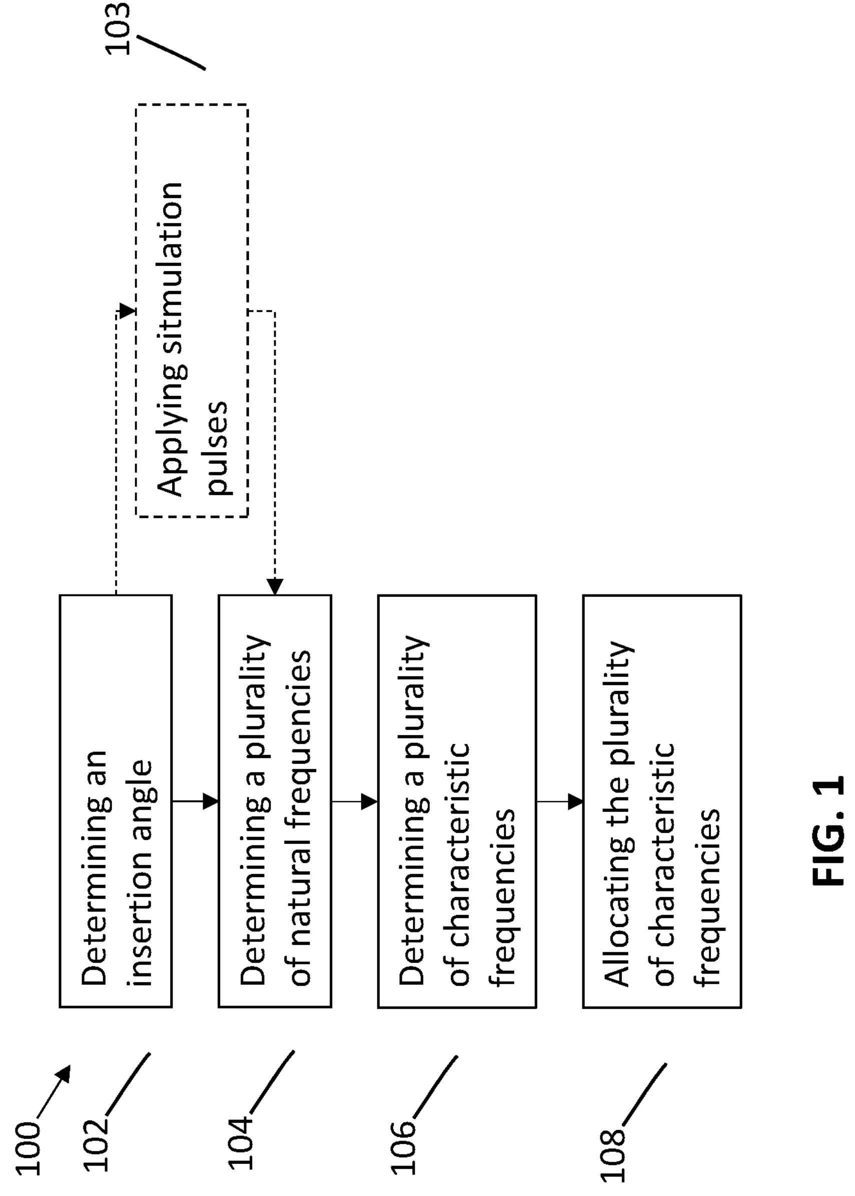
FIG. 1 illustrates a method of fitting a cochlea implant system.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, etc. (collectively referred to as “elements”). Depending upon particular application, design constraints or other reasons, these elements may be implemented using other equivalent elements.

The hearing aid that is adapted to improve or augment the hearing capability of a user by receiving an acoustic signal from a user’s surroundings, generating a corresponding audio signal, possibly modifying the audio signal and providing the possibly modified audio signal as an audible signal to at least one of the user’s ears. Such audible signals may be provided in the form of an acoustic signal transferred as mechanical vibrations to the user’s inner ears through bone structure of the user’s head.

The hearing aid is adapted to be worn in any known way. This may include arranging a unit of the hearing aid attached to a fixture implanted into the skull bone such as in a Bone Anchored Hearing Aid or at least a part of the hearing aid may be an implanted part.

A “hearing system” or a “cochlea implant system” refers to a system comprising one or two hearing aids, one or two cochlea implants, and a “binaural hearing system” refers to a system comprising two hearing aids or two cochlea implant where the devices are adapted to cooperatively provide audible signals to both of the user’s ears or the hearing aid of bone conduction type or an acoustical hearing aid may be part of a bimodal system comprising a cochlea implant and a hearing aid or a bone conduction hearing aid. The system may further include an external device(s) that communicates with at least one hearing aid, the external device affecting the operation of the hearing aids and/or benefitting from the functioning of the hearing aids. A wired or wireless communication link between the at least one hearing aid and the external device is established that allows for exchanging information (e.g. control and status signals, possibly audio signals) between the at least one hearing aid and the external device. Such external devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing aid. The remote control is adapted to control functionality and operation of the at least one hearing aids. The function of the remote control may be implemented in a SmartPhone or other electronic device, the SmartPhone/electronic device possibly running an application that controls functionality of the at least one hearing aid.

In general, a hearing aid or a cochlea implant includes i) an input unit such as a microphone for receiving an acoustic signal from a user’s surroundings and providing a corresponding input audio signal, and/or ii) a receiving unit for electronically receiving an input audio signal. The hearing aid further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user’s environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer for providing mechanical vibrations either transcutaneously or percutaneously to the skull bone.

FIG. 1 illustrates a method 100 of fitting a cochlea implant system 200 to a patient. The method comprising determining 102 an insertion angle of at least one electrode of a first electrode array of the cochlea implant system inserted into a cochlea of the patient, determining 104 a plurality of natural frequencies as a function of a cochlea spiral length based on a natural frequency allocation model and the insertion angle, 106 determining a plurality of characteristic frequencies as a function of a cochlea spiral length by frequency downshifting the plurality of natural frequencies until an objective is obtained and while preserving the harmonic relationship between the natural frequencies of the plurality of natural frequencies in the plurality of characteristic frequencies, and allocating 108 the plurality of characteristic frequencies to each electrode of the first electrode array based on the insertion angle of the at least one electrode.

The method 100 may further comprise determining 102 an insertion angle for each of the electrodes of the first electrode array based on the insertion angle determined for the at least one electrode, and determining 104 the plurality of natural frequencies as a function of a cochlea spiral length by mapping the insertion angle of each electrodes of the first electrode to a physiological model.

The method 100 may further comprise determining 102 an insertion angle of at least another electrode of a second electrode array of the cochlea implant system inserted into another cochlea of the patient, applying 103 a stimulation pulse to at least one electrode of the first electrode array and the second electrode array for determining a binaural interaction component of the patient, and determining 104 the plurality of natural frequencies as a function of a cochlea spiral length based on the binaural interaction component.

The method 100 may further comprise determining 102 an insertion angle of at least another electrode of a second electrode array of the cochlea implant system inserted into another cochlea of the patient, applying 103 a stimulation pulse to at least one electrode of the first electrode array and the second electrode array for determining an interaural pulse time difference sensitivity or an interaural pitch matching, and determining 104 the plurality of natural frequencies as a function of a cochlea spiral length based on the interaural pulse time difference sensitivity or the interaural pitch matching.

Figures 2A, 2B:
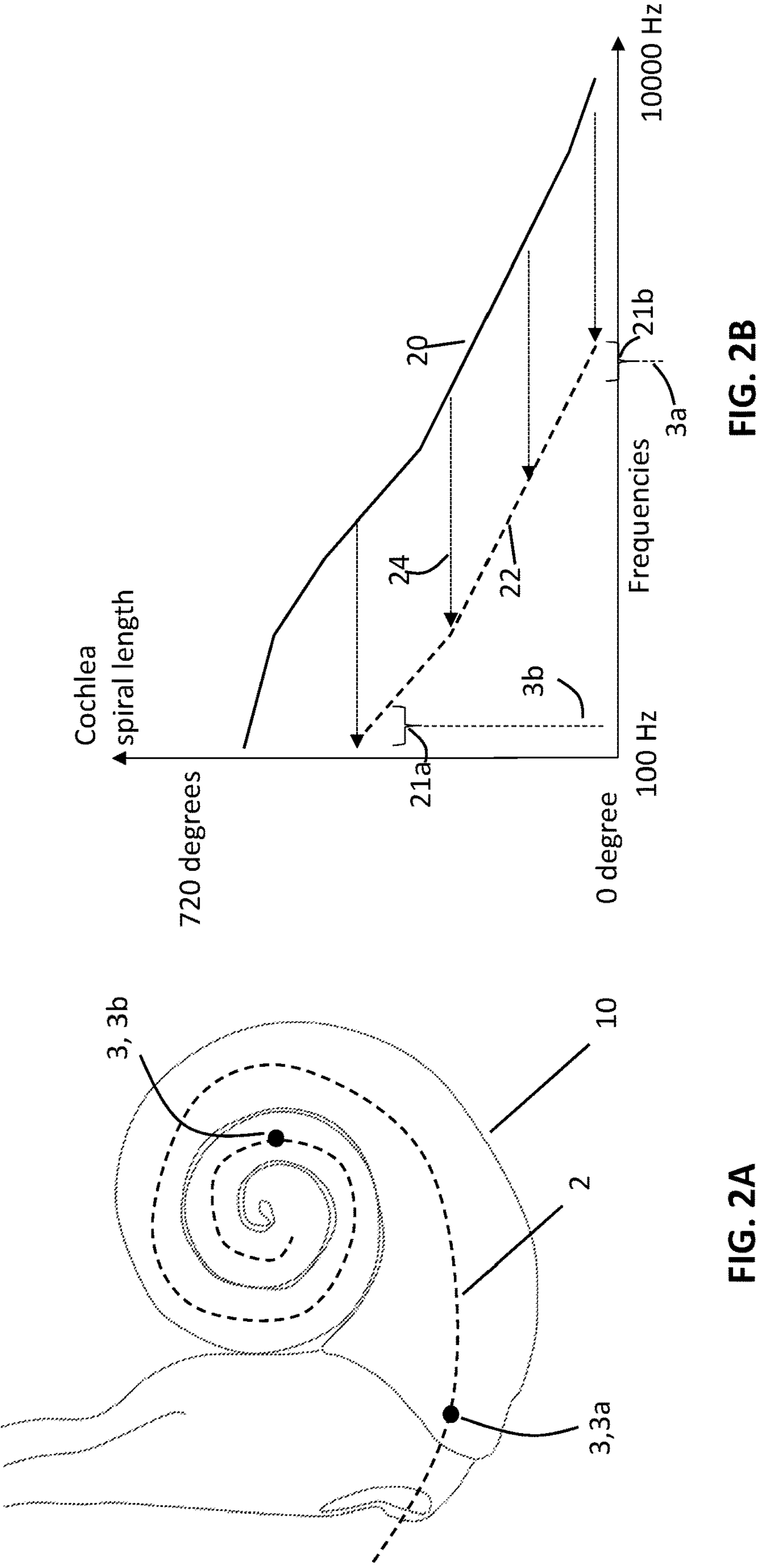
FIGS. 2A and 2B illustrate location of an electrode array and frequency downshifting of a plurality of natural frequencies.

FIG. 2A illustrates an example of a location of an electrode array 2 within a cochlea 10 of a patient of the cochlea implant system, for example the first electrode array or the second electrode array. In this specific example, a most basal electrode 3*a* and a most apical electrode 3*b* are seen within the cochlea 10. In this example, the insertion angle may be determined for either the most apical electrode 3*b* or the most basal electrode 3*a*. It could be any electrodes 3 of the electrode for which the insertion angle is to be determined. FIG. 2B illustrates an example of frequency downshifting 24 the plurality of natural frequencies 20 for determine the plurality of characteristic frequencies 22. The frequency range which is covered by the electrode array 2 is determined by the location of the electrode array 2 within the cochlea 10. In this example, a lowest frequency range 21*a* of the plurality of characteristic frequencies 22 is allocated to the most apical electrode 3*b*, and the highest frequency range 21*b* of the plurality of characteristic frequencies 22 is allocated to the most basal electrode 3*a* arranged within the cochlea 10. The remaining electrodes 3 of the electrode array 2 may be allocated with the remaining frequency ranges (21, not shown) of the plurality of characteristic frequencies 22 based on the insertion angle.

Table 1 discloses different examples of placement of the most apical electrode 3*b* within the cochlea 10. When the insertion angle of the most apical electrode 3*b* is 525° the minimum natural frequency allocated to the electrode 3*b* is 300 Hz. That means, the most apical electrode array does not cover the frequency range from below 300 Hz. When the insertion angle of the most apical electrode 3*b* is 417° the minimum natural frequency allocated to the electrode 3*b* is 500 Hz. That means, the most apical electrode array does not cover the frequency range from below 500 Hz. When the insertion angle of the most apical electrode 3*b* is 358° the minimum natural frequency allocated to the electrode 3*b* is 900 Hz. That means, the most apical electrode array does not cover the frequency range from below 900 Hz.

TABLE 1

| Insertion angle of the most apical electrode | Determined natural frequency of the most apical electrode | Frequencies which the electrode array does not cover |
|---|---|---|
| 525° | 300 Hz | <300 Hz |
| 417° | 500 Hz | <500 Hz |
| 358° | 900 Hz | <900 Hz |

The amount of frequency downshifting is then determined by a ratio 1/N which which is then multiplied with the plurality of natural frequencies (20, $fn_{c0}$) for determine the plurality of characteristic frequencies (22, $fci_{c0}$).

$$fci_{c0} = \frac{fn_{c0}}{N}$$

Table 2 illustrates an example where the natural frequencies of the most apical electrode 3*b* is downshifted with a ratio of between ⅓ to ½ for obtaining a minimum characteristic frequency of between 100 Hz to 150 Hz, respectively, when the insertion angle of the most apical electrode is 525°. The same is seen for when the insertion angle is 417° and 358°, but with an increasing ratio 1/N as the insertion angle of the most apical electrode 3*b* reduces.

TABLE 2

| Insertion angle of the most apical electrode | Determined minimum characteristic frequency of the most apical electrode | Amount of frequency downshifting |
|---|---|---|
| 525° | 100 Hz to 150 Hz | N = 3, 2 |
| 417° | 100 Hz to 250 Hz | N = 5, 4, 3, 2 |
| 358° | 100 Hz to 180 Hz | N = 9, 8, 7, 6, 5 |

Figure 3:
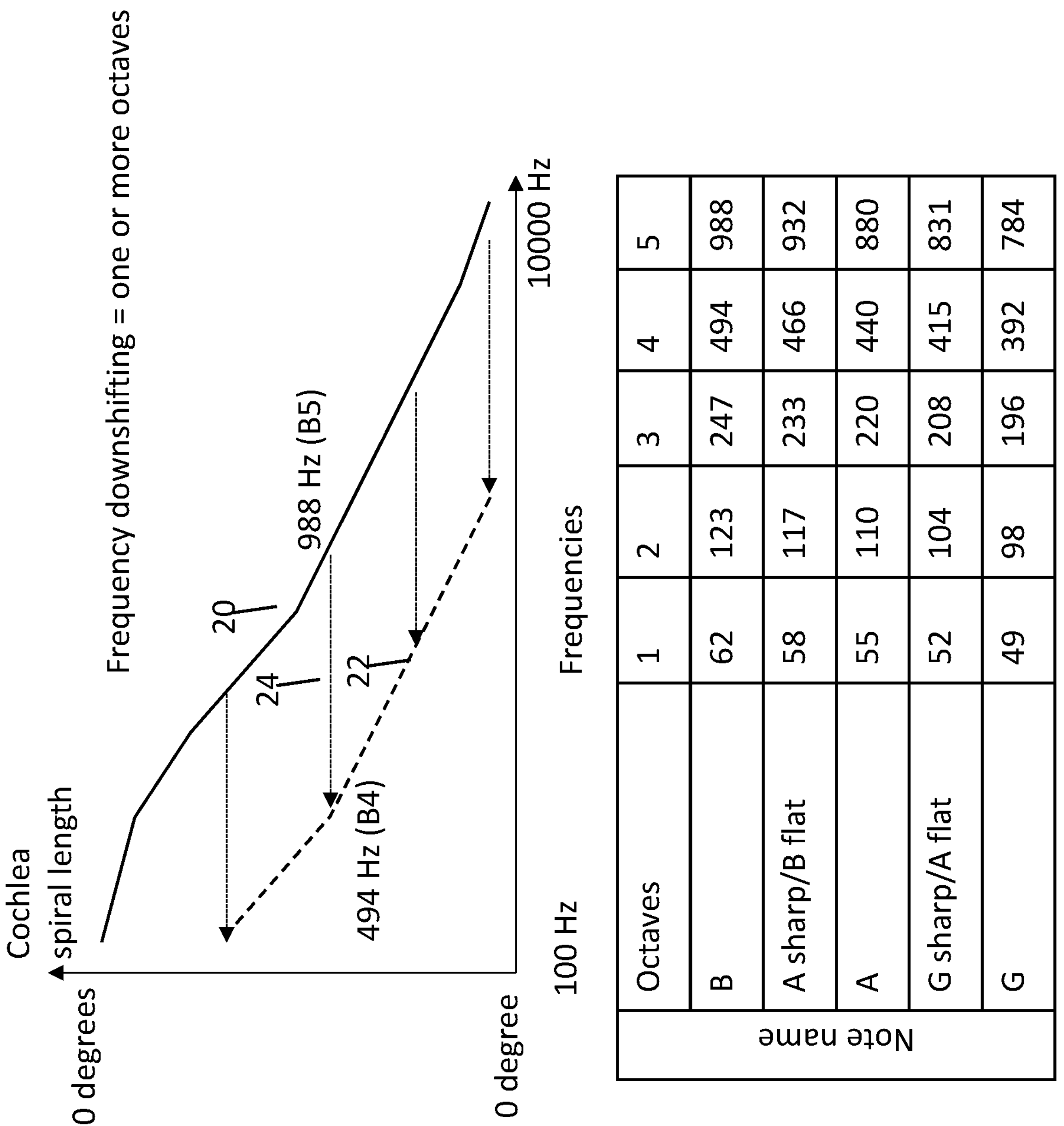
FIG. 3 illustrates frequency downshifting of a plurality of natural frequencies.

FIG. 3 illustrate an example where the frequency downshifting 24 corresponds to one or more octaves. The frequency downshifting 24 results in an octave shift in frequencies from one electrode to another electrode, e.g. neighboring electrodes of the electrode array. In this example, the frequency downshifting corresponds to a single octave, which for example means, that note 'B5' is downshifted to note 'B4' for a given electrode 2. In another example, the frequency downshifting could be two octaves, which means, that note 'B5' is downshifted to note 'B3', and soon.

Figure 4A:
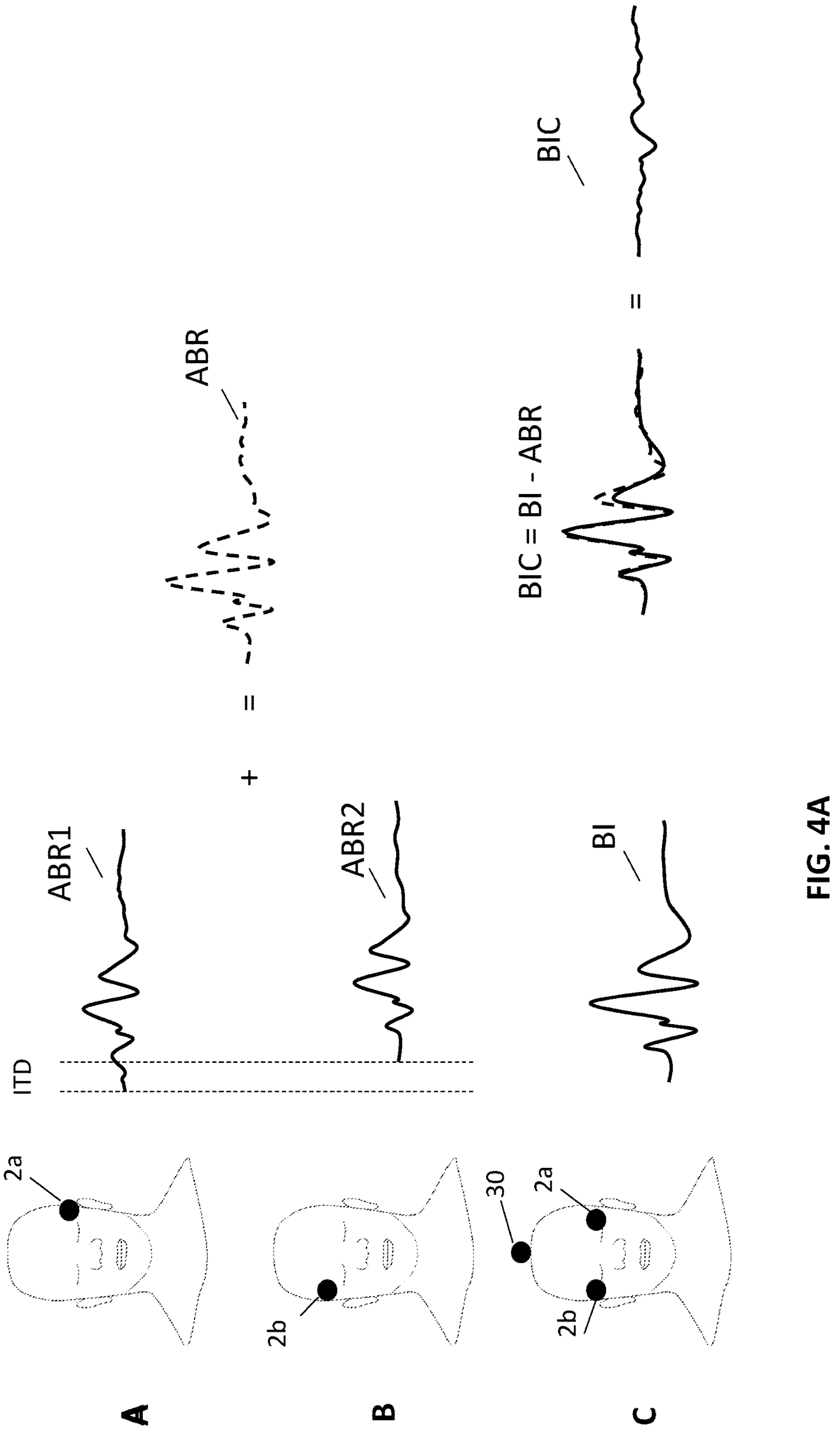
Figure 4B:
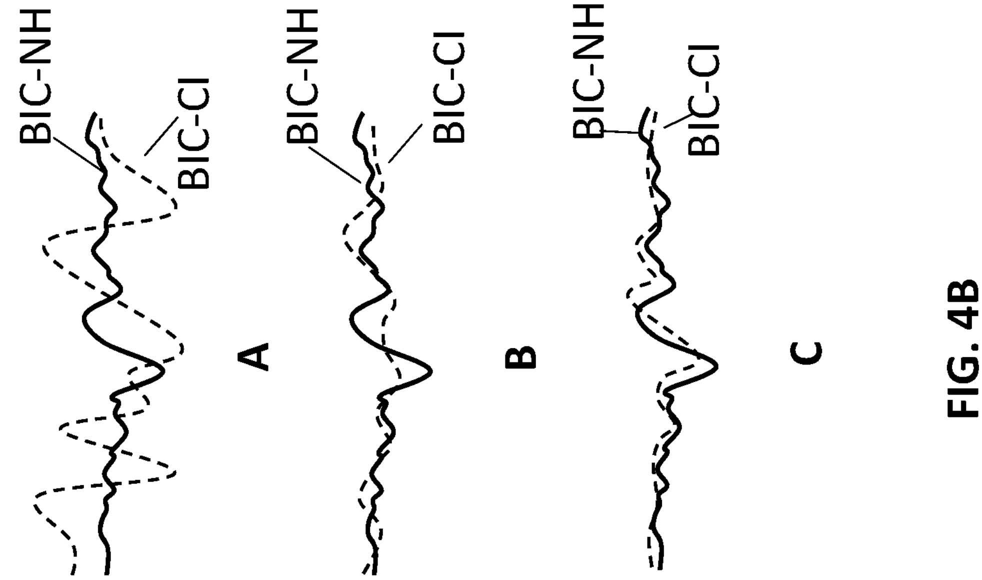

FIGS. 4A and 4B disclose an example of how to determine a binaural interaction component of the patient, and to determine the plurality of natural frequencies as a function of a cochlea spiral length based on the binaural interaction component. FIG. 4A, scene A, illustrates a fitting situation where a first auditory brainstem response ABR1 is recorded by a recording electrode of the first electrode array when applying a first stimulation to the first cochlea by a stimulating electrode of the first electrode array 2*a*. In scene B, a second auditory brainstem response ABR2 is recorded by a recording electrode of the second electrode array 2*b* (or an electrode probe) when applying a second stimulation to the second cochlea by a stimulating electrode of the second electrode array 2*b*. Or, in scene B, a second auditory brainstem response ABR2 is recorded by a recording probe applied into an ear channel of an opposite ear to where the electrical stimulation is applied when applying an acoustical stimulation to the second cochlea by a speaker of a hearing aid. The second stimulation or the acoustical stimulation should be applied after a time period from a stimulation time of when the first stimulation was applied by the first stimulation electrode. A summed auditory brainstem response ABR is determined by summing the first brainstem response ABR1 and the second auditory brainstem response ABR2. Alternatively, the second auditory brainstem response ABR2 may be time-shifted in relation to the first auditory brainstem with an interaural time difference ITD before the summation. Then, a binaural waveform BI is recorded by the first and the second electrode array (2*a*, 2*b*), or by the first electrode array and a microphone of the hearing aid, or by an external electrode 30 applied on the top of the head and in-between the ears of the head of the patient when applying simultaneously a stimulation pulse via the stimulating electrode of both the first and the second electrode array (2*a*, 2*b*) or when applying simultaneously the stimulation pulse and the acoustical stimulation. Binaural interaction component BIC is determined by subtracting the binaural waveform BI with the summed auditory brainstem response ABR. The external electrode may be an EEG electrode 30.

FIG. 4B illustrates an example of where the plurality of characteristic frequencies is determined for each of the electrode arrays (2*a*, 2*b*) for obtaining a binaural interaction component BIC-CI for the patient which is similar or comparable to a binaural interaction component BIC-NH of a normal hearing. In scene A of FIG. 4B it is seen a poor match between BIC-CI and BIC-NH for a given amount of frequency downshifting of the plurality of natural frequencies for both electrode arrays (2*a*, 2*b*) or for only first electrode array 2*a*. In scene B of FIG. 4B, a better match between BIC-CI and BIC-NH for a given amount of frequency downshifting is seen, and scene C of FIG. 4B, illustrates an acceptable match between BIC-CI and BIC-NH for a given amount of frequency downshifting, An acceptable match criterion of the match may be determined by a standard deviation function, such as a root mean square function. The acceptable match criterion of match may be determined by harmonic relations between local maxima appearing in the BIC-CI.

The amount of frequency downshifting may be the same or different between the electrode arrays (2*a*, 2*b*).

Figure 5C:
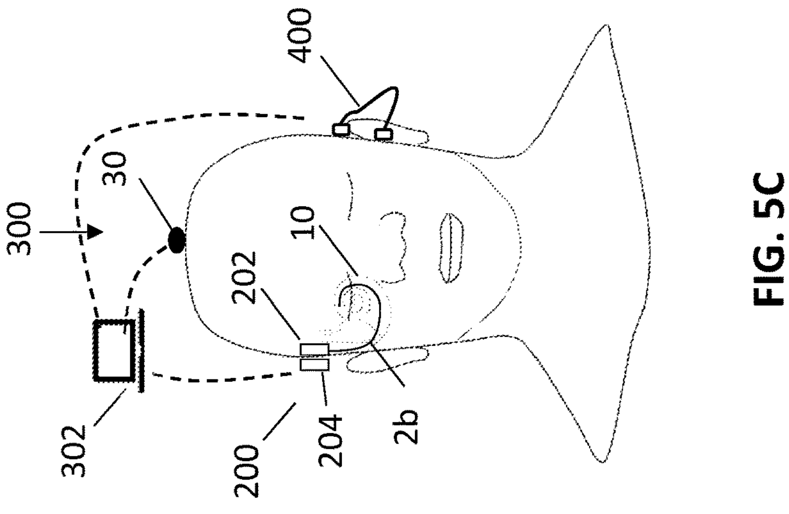
FIGS. 5A, 5B and 5C illustrate different examples of a system for fitting a cochlea implant system.
Figure 5B:
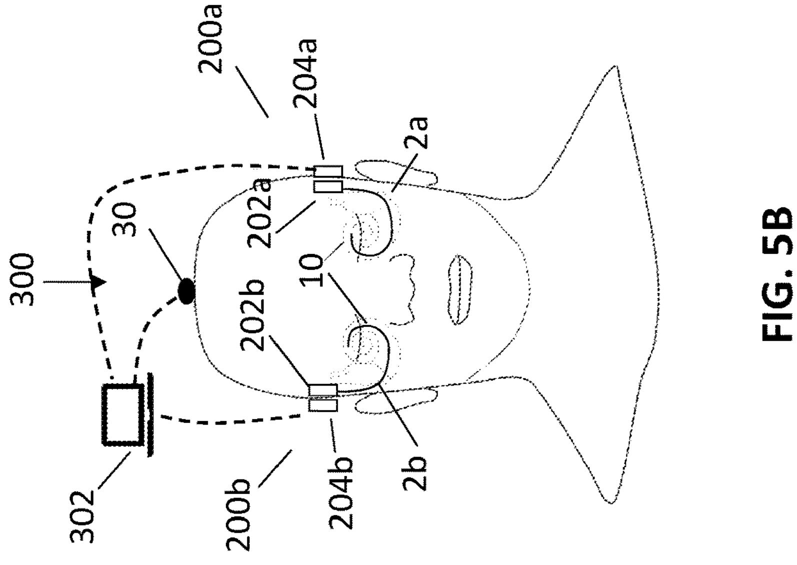
Figure 5A:
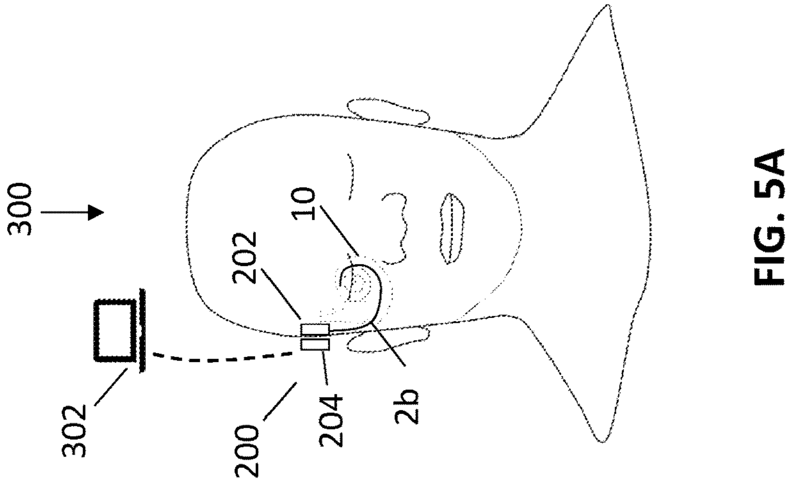

FIGS. 5A and 5B illustrate a system 300 for fitting the cochlea implant system 200 to a patient. In this specific example, the system 300 comprising a first implantable stimulation unit 202 with a first electrode array 2*b* including a plurality of electrodes 3 configured to apply an electrical stimulation to auditory nerve fibers of the cochlea 10 of the patient. The system for comprises an external unit (204, 302) including a memory unit 208 which comprises a natural frequency allocation model. In this example the external unit can be a fitting computer 300 and/or a sound processor 204 which is either applied on the head of the user or implanted together with the implantable stimulation unit 202. The system comprises a frequency allocating unit 210 configured to allocate a plurality of characteristic frequencies 22 to each electrode 3 of the first electrode array 2*b* according to a frequency allocating scheme, wherein the frequency allocating scheme including. The frequency allocation unit may be arranged within the fitting computer 302 and/or the sound processor 204. The frequency allocation scheme includes;

- determining an insertion angle of at least one electrode of the first electrode array 2*b*,
- determining a plurality of natural frequencies 20 as a function of a cochlea spiral length based on the natural frequency allocation model and the insertion angle,
- determining the plurality of characteristic frequencies 22 as a function of a cochlea spiral length by frequency downshifting 24 the plurality of natural frequencies 20 until an objective is obtained and while preserving the harmonic relationship between the natural frequencies of the plurality of natural frequencies 20 in the plurality of characteristic frequencies 22, and
- allocating the plurality of characteristic frequencies 22 to each electrode 3 of the first electrode array 2*b* based on the insertion angle of the at least one electrode (3, 3*a*, 3*b*).

In FIG. 5A, the fitting computer 302 is connected to the cochlea implant system 200 if the method 100 is performed by the fitting computer 302, and in the other case where the method 100 is performed by the cochlea implant system 200 the connection to the fitting computer 302 is not necessary. Similar goes for the system 300 illustrated in FIGS. 5B and 5C.

In FIG. 5B the system 300 comprises a first cochlea implant system 200*a*, a second cochlea implant system 200*b* and optionally an EEG electrode 30 connected to a fitting computer 302. The system 300 is configured for determine the binaural interaction component BIC of the patient in a bilateral setup. The method of fitting the cochlea implant systems is described in FIGS. 4A and 4B.

In FIG. 5C the system 300 comprises a first cochlea implant system 200*a*, a hearing aid 400 and optionally an EEG electrode 30 connected to a fitting computer 302. The system 300 is configured for determine the binaural interaction component BIC of the patient in a bimodal setup. The method of fitting the cochlea implant systems is described in FIGS. 4A and 4B.

Figure 6:
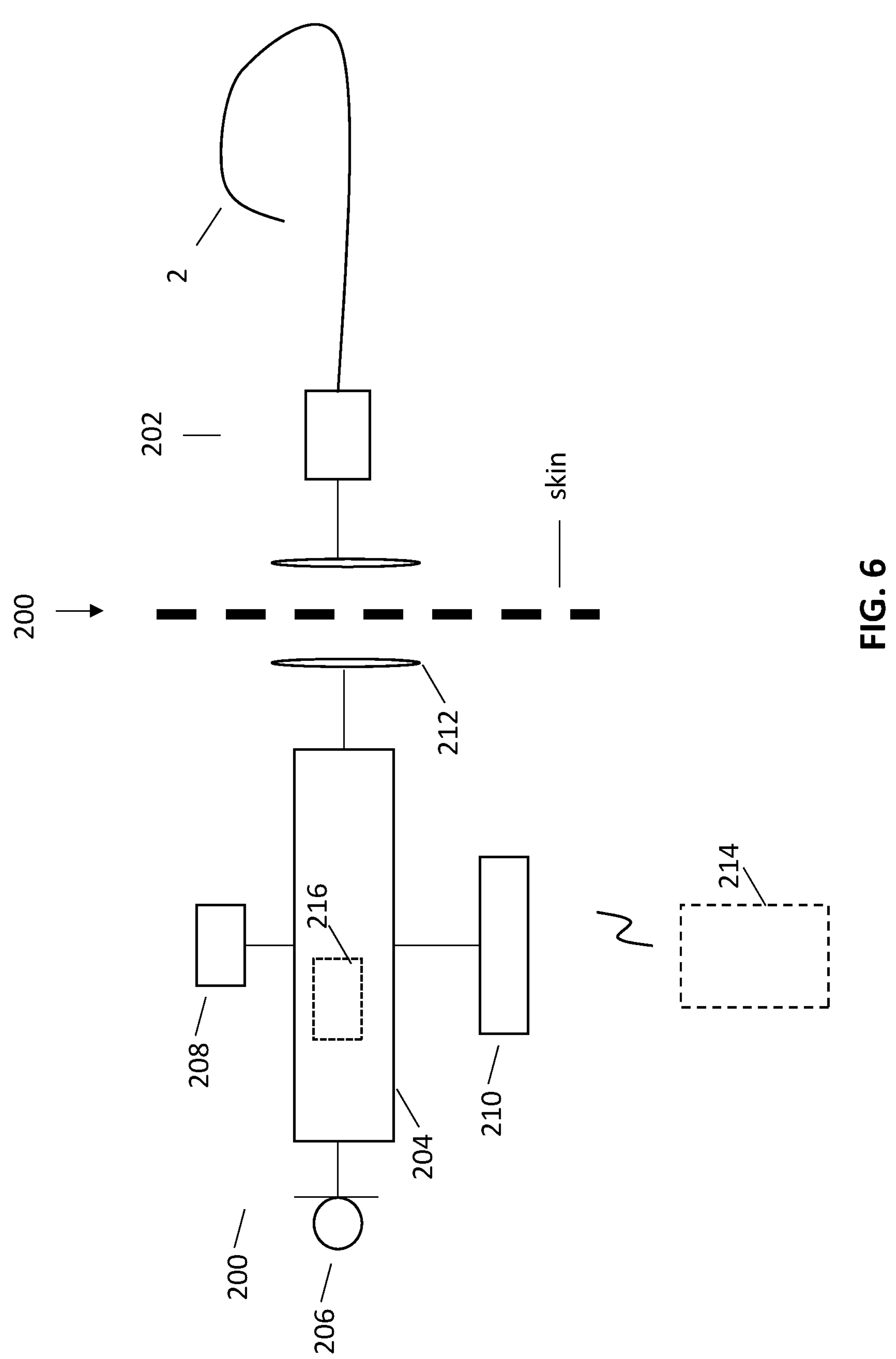
FIG. 6 illustrate a cochlea implant system.

FIG. 6 illustrates the cochlea implant system 200 which includes the sound processor 204, a microphone 206, the memory unit 208, the frequency allocation unit 210 and a transcutaneous radio frequency link 212 configured to inductively communicate with an implantable stimulation unit 202 which is connected to the electrode array 2. In this present example, the cochlea implant system is configured to continuously adapt the plurality of characteristic frequencies by dynamically changing the objective. The objective may be depended on the acoustic signal or a sound processing program of the cochlea implant system. The sound processing program may be set by an external device 214, e.g. a smartphone which is wirelessly connected to the cochlea implant system 200. Thereby, the electrode array of the cochlea implant system will always have an optimal frequency allocation in relation to the acoustical input received by the microphone unit 206 or an RF antenna (not shown). The microphone unit 206 may include one or more microphones.

The cochlea implant system 300 includes a filter bank 216 configured to generate multiple audio bands, where each multiple audio band is mapped to each electrode 3 of the electrode array 2, and where a frequency range of each of the multiple audio bands includes at least the plurality of characteristic frequencies 22 allocated to the respective mapped electrode 3.

As used, the singular forms “a,” “an,” and “the” are intended to include the plural forms as well (i.e. to have the meaning “at least one”), unless expressly stated otherwise. It will be further understood that the terms “includes,” “comprises,” “including,” and/or “comprising,” when used in this specification, specify the presence of stated features, elements, components, and/or steps but do not preclude the presence or addition of one or more other features, elements, components, and/or steps thereof. It will also be understood that when an element is referred to as being “connected” or “coupled” to another element, it can be directly connected or coupled to the other element, but an intervening element may also be present, unless expressly stated otherwise. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The scope should be judged in terms of the claims that follow.

The invention claimed is:

1. A method of fitting a cochlea implant system to a patient, said method comprising:

determining an insertion angle of at least one electrode of a first electrode array of the cochlea implant system inserted into a cochlea of the patient, determining a plurality of natural frequencies as a function of a cochlea spiral length based on a natural frequency allocation model and the insertion angle, determining a plurality of characteristic frequencies as a function of a cochlea spiral length by frequency downshifting the plurality of natural frequencies until a predetermined frequency allocation objective is obtained while preserving the harmonic relationship between the natural frequencies of the plurality of natural frequencies in the plurality of characteristic frequencies, and programming the cochlea implant system to allocate the plurality of characteristic frequencies to each electrode of the first electrode array based on the insertion angle of the at least one electrode.

2. A method of fitting a cochlea implant system according to claim 1, wherein the predetermined frequency allocation objective is at least one of:

a first range of characteristic frequencies between 100 Hz and 250 Hz is allocated to a most apical electrode of the first electrode array, a second range of characteristic frequencies between 6600 Hz and 7700 Hz is allocated to a most basal electrode of the first electrode array, or the frequency downshifting of the plurality of natural frequencies corresponds to an octave.

3. A method of fitting a cochlea implant system according to claim 2, wherein an amount of frequency downshifting relates to an insertion angle of a most apical electrode and the predetermined frequency allocation objective.

4. A method of fitting a cochlea implant system according to claim 2, wherein:

when the insertion angle of the most apical electrode is, about 525 degrees, the frequency downshifting of the plurality of natural frequencies to the plurality of characteristic frequencies is between ⅓ to ½, when the insertion angle of the most apical electrode is about 417 degrees, the frequency downshifting of the plurality of natural frequencies to the plurality of characteristic frequencies is between ⅕ to ½, and when the insertion angle of the most apical electrode is about 358 degrees, the frequency downshifting of the plurality of natural frequencies to the plurality of characteristic frequencies is between ⅙ to ⅕.

5. A method of fitting a cochlea implant system according to claim 2, comprising;

determining an insertion angle for each of the electrodes of the first electrode array based on the insertion angle determined for the at least one electrode, and determining the plurality of natural frequencies as a function of a cochlea spiral length by mapping the insertion angle of each electrodes of the first electrode to a physiological model.

6. A method of fitting a cochlea implant system according to claim 1, wherein an amount of frequency downshifting relates to an insertion angle of a most apical electrode and the predetermined frequency allocation objective.

7. A method of fitting a cochlea implant system according to claim 6, wherein:

when the insertion angle of the most apical electrode is, about 525 degrees, the frequency downshifting of the plurality of natural frequencies to the plurality of characteristic frequencies is between ⅓ to ½, when the insertion angle of the most apical electrode is about 417 degrees, the frequency downshifting of the plurality of natural frequencies to the plurality of characteristic frequencies is between ⅕ to ½, when the insertion angle of the most apical electrode is about 358 degrees, the frequency downshifting of the plurality of natural frequencies to the plurality of characteristic frequencies is between ⅙ to ⅕.

8. A method of fitting a cochlea implant system according to claim 6, comprising;

determining an insertion angle for each of the electrodes of the first electrode array based on the insertion angle determined for the at least one electrode, and determining the plurality of natural frequencies as a function of a cochlea spiral length by mapping the insertion angle of each electrodes of the first electrode to a physiological model.

9. A method of fitting a cochlea implant system according to claim 1, wherein:

when the insertion angle of the most apical electrode is, about 525 degrees, the frequency downshifting of the plurality of natural frequencies to the plurality of characteristic frequencies is between ⅓ to ½, when the insertion angle of the most apical electrode is 417 degrees, the frequency downshifting of the plurality of natural frequencies to the plurality of characteristic frequencies is between ⅕ to ½, and when the insertion angle of the most apical electrode is 358 degrees, the frequency downshifting of the plurality of natural frequencies to the plurality of characteristic frequencies is between ⅙ to ⅕.

10. A method of fitting a cochlea implant system according to claim 1, comprising:

determining an insertion angle for each of the electrodes of the first electrode array based on the insertion angle determined for the at least one electrode, and determining the plurality of natural frequencies as a function of a cochlea spiral length by mapping the insertion angle of each electrodes of the first electrode to a physiological model.

11. A method of fitting a cochlea implant system according to claim 1, wherein the method comprising:

determining an insertion angle of at least another electrode of a second electrode array of the cochlea implant system inserted into another cochlea of the patient, applying a stimulation pulse to at least one electrode of the first electrode array and the second electrode array simultaneously and time shifted for determining a binaural interaction component of the patient, and determining the plurality of natural frequencies as a function of a cochlea spiral length based on the binaural interaction component.

12. A method of fitting a cochlea implant system according to claim 1, wherein the method comprising:

determining an insertion angle of at least another electrode of a second electrode array of the cochlea implant system inserted into another cochlea of the patient, applying a stimulation pulse to at least one electrode of the first electrode array and the second electrode array for determining an interaural pulse time difference sensitivity or an interaural pitch matching, and determining the plurality of natural frequencies as a function of a cochlea spiral length based on the interaural pulse time difference sensitivity or the interaural pitch matching.

13. A system for fitting a cochlea implant system to a patient comprising:

a first implantable stimulation unit with a first electrode array including a plurality of electrodes configured to apply an electrical stimulation to auditory nerve fibers of a cochlea of the patient;

an external unit including a memory unit which comprises a natural frequency allocation model; and a frequency allocating unit configured to allocate a plurality of characteristic frequencies to each electrode of the first electrode array according to a frequency allocating scheme, wherein the frequency allocating scheme including;

determining an insertion angle of at least one electrode of the first electrode array, determining a plurality of natural frequencies as a function of a cochlea spiral length based on the natural frequency allocation model and the insertion angle, determining the plurality of characteristic frequencies as a function of a cochlea spiral length by frequency downshifting the plurality of natural frequencies until a predetermined frequency allocation objective is obtained and while preserving the harmonic relationship between the natural frequencies of the plurality of natural frequencies in the plurality of characteristic frequencies, and programming the cochlea implant system to allocate the plurality of characteristic frequencies to each electrode of the first electrode array based on the insertion angle of the at least one electrode.

14. A system for fitting a cochlea implant system according to claim 13, comprising a filter bank configured to generate multiple audio bands, where each multiple audio band is mapped to each electrode of the electrode array, and where a frequency range of each of the multiple audio bands includes at least the plurality of characteristic frequencies allocated to the respective mapped electrode.

15. A system for fitting a cochlea implant system according to claim 13, wherein the predetermined frequency allocation objective is at least one of:

a first range of characteristic frequencies between 100 Hz and 25 0 Hz is allocated to a most apical electrode of the first electrode array, a second range of characteristic frequencies between 6600 Hz and 8100 Hz is allocated to a most basal electrode of the first electrode array, or the frequency downshifting of the plurality of natural frequencies corresponds to an octave.

16. A system for fitting a cochlea implant system according to claim 13, wherein an amount of frequency downshifting relates to an insertion angle of a most apical electrode and the predetermined frequency allocation objective.

17. A system for fitting a cochlea implant system according to claim 16, wherein:

when the insertion angle of the most apical electrode is about 525 degrees, the frequency downshifting of the plurality of natural frequencies to the plurality of characteristic frequencies is between ⅓ to ½, when the insertion angle of the most apical electrode is about 417 degrees, the frequency downshifting of the plurality of natural frequencies to the plurality of characteristic frequencies is between ⅕ to ½, and when the insertion angle of the most apical electrode is about 358 degrees, the frequency downshifting of the plurality of natural frequencies to the plurality of characteristic frequencies is between ⅙ to ⅕.

18. A system for fitting a cochlea implant system according to claim 13, wherein the plurality of natural frequencies as a function of a cochlea spiral length is determined by mapping the position of each electrodes of the first electrode array based on the determined insertion angle of the at least one electrode to a physiological model.

19. A system for fitting a cochlea implant system according to claim 13, comprising a second implantable stimulation unit with a second electrode array including a plurality of electrodes configured to apply an electrical stimulation to auditory nerve fibers of another cochlea of the patient, and wherein the frequency allocating scheme including:

determining an insertion angle of at least another electrode of a second electrode array of the cochlea implant system inserted into another cochlea of the patient, applying a stimulation pulse to at least one electrode of the first electrode array and the second electrode array simultaneously and time shifted for determining a binaural interaction component of the patient, and determining the plurality of natural frequencies as a function of a cochlea spiral length based on the binaural interaction component.

20. A system for fitting a cochlea implant system according to claim 13, comprising a hearing aid configured to apply an acoustical stimulation to auditory nerve fibers of another cochlea of the patient, and wherein the frequency allocating scheme including:

applying a stimulation pulse to at least one electrode of the first electrode array and an acoustical stimulation to the another cochlea via the hearing aid simultaneously and time shifted for determining a binaural interaction component of the patient, determining the plurality of natural frequencies as a function of a cochlea spiral length based on the natural frequency allocation model, the binaural interaction component, and the insertion angle, determining the plurality of characteristic frequencies as a function of a cochlea spiral length by frequency downshifting the plurality of natural frequencies until a predetermined frequency allocation objective is obtained and while preserving the harmonic relationship between the natural frequencies of the plurality of natural frequencies in the plurality of characteristic frequencies, and programming the cochlea implant system to allocate the plurality of characteristic to each electrode of the first electrode array, respectively.

* * * * *